United States Patent [19]

Piche et al.

[11] Patent Number: 4,754,645
[45] Date of Patent: Jul. 5, 1988

[54] ULTRASONIC CHARACTERIZATION OF POLYMERS UNDER SIMULATED PROCESSING CONDITIONS

[75] Inventors: Luc Piche; Francoise Massines, both of Montreal; André Hamel, St-Hubert; Christian Neron, Boucherville, all of Canada

[73] Assignee: Canadian Patents and Development Limited, Ottawa, Canada

[21] Appl. No.: 49,579

[22] Filed: May 14, 1987

[51] Int. Cl.$^4$ ............................................. G01N 29/00
[52] U.S. Cl. ........................................ 73/597; 73/599; 73/644
[58] Field of Search ................. 73/597, 599, 629, 632, 73/644, 571

[56] References Cited

U.S. PATENT DOCUMENTS

| | | | |
|---|---|---|---|
| 3,316,755 | 5/1967 | Ensley | 73/597 |
| 3,350,923 | 11/1967 | Cross | 73/644 |
| 3,858,437 | 1/1975 | Jarzynski et al. | 73/597 |
| 4,346,599 | 8/1982 | McLaughlin et al. | 73/597 |
| 4,509,360 | 4/1985 | Erwin et al. | 73/599 |

OTHER PUBLICATIONS

H. A. Waterman, *Kolloid-Zeitschrift & Zeitschrift fur Polymere*, vol. 192, #1-2 (Oct. 1963), pp. 1-8.
B. Hartmann et al., "Immersion Apparatus for Ultrasonic Measurements in Polymers", *J. Acoust. Soc. Am.*, v. 56, No. 5 (Nov. 1974), pp. 1469-1477.
G. W. Paddison, "An Ultrasonic Immersion Apparatus for the Determination of High-Frequency Storage and Loss Moduli for Polymers and Polymeric Composites", Proc. IEEE Ultrasonics Symposium, 502-506 (1979).
H. J. McSkimin, "Ultrasonic Methods for Measuring the Mechanical Properties of Liquids and Solids", *Physical Acoustics*, ed. by W. P. Mason, Academic Press, New York (1964), vol. I-A, Chap. 4, pp. 271-334.
J. R. Asay et al., "Pressure and Temperature Dependence of the Acoustic Velocities in Polymethylmethacrylate", *J. Appl. Phys.*, 40, 4 (Mar. 1969), pp. 1768-1783.
D. L. Lamberson et al., "Equation of State of Polystyrene and Polymethylmethacrylate from Ultrasonic Measurements at Moderate Pressures", *J. Appl. Phys.*, 43, 3 (Mar. 1972), pp. 976-985.

*Primary Examiner*—John Chapman
*Attorney, Agent, or Firm*—Swabey, Mitchell, Houle, Marcoux & Sher

[57] ABSTRACT

A method and an apparatus for ultrasonically characterizing polymer materials under simulated processing conditions are disclosed. According to the invention, a sample of a polymer is held in confinement between two axially aligned buffer rods having opposed parallel end surfaces spaced from one another to define a gap filled with the polymer sample, the polymer sample being acoustically coupled to the opposed end surfaces of the buffer rods. Ultrasonic waves are transmitted through one of the buffer rods in a direction toward the polymer sample for interaction therewith, and the polymer sample is subjected to controlled temperature or pressure variations over a predetermined period of time, the variation in temperature or pressure being effected via the buffer rods. Phase and amplitude variations of the ultrasonic waves having interacted with the polymer sample are continuously monitored as well as thickness variations of the polymer sample, over the predetermined period of time, to obtain data comprising phase, amplitude and thickness values measured as a function of temperature or pressure and time, which are then processed to derive characteristic parameters providing both a thermodynamic and viscoelastic characterization of the polymer. The present invention enables one to more adequately control the polymer processing conditions, with a view to optimizing the properties of a given polymer for a given application.

20 Claims, 9 Drawing Sheets

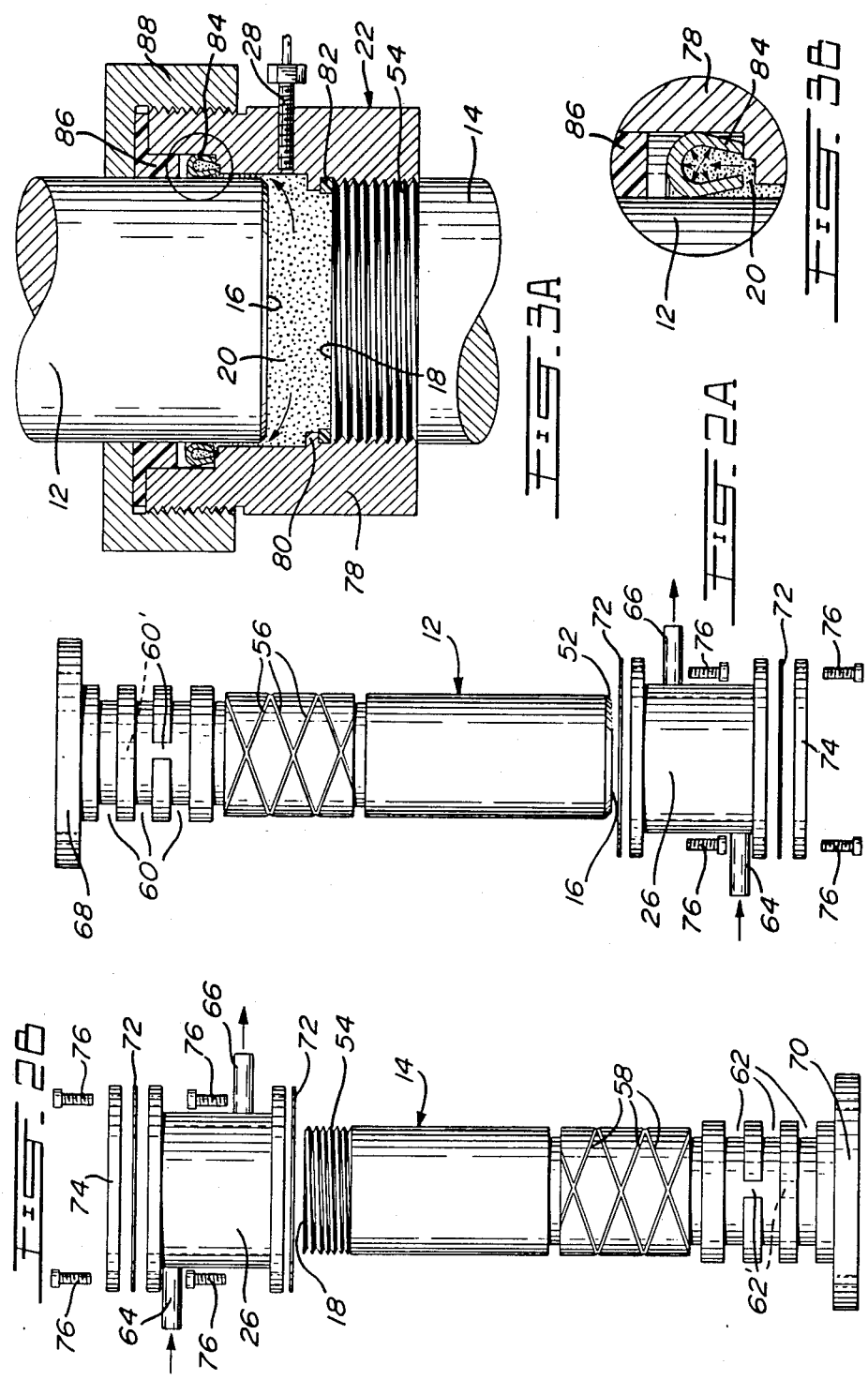

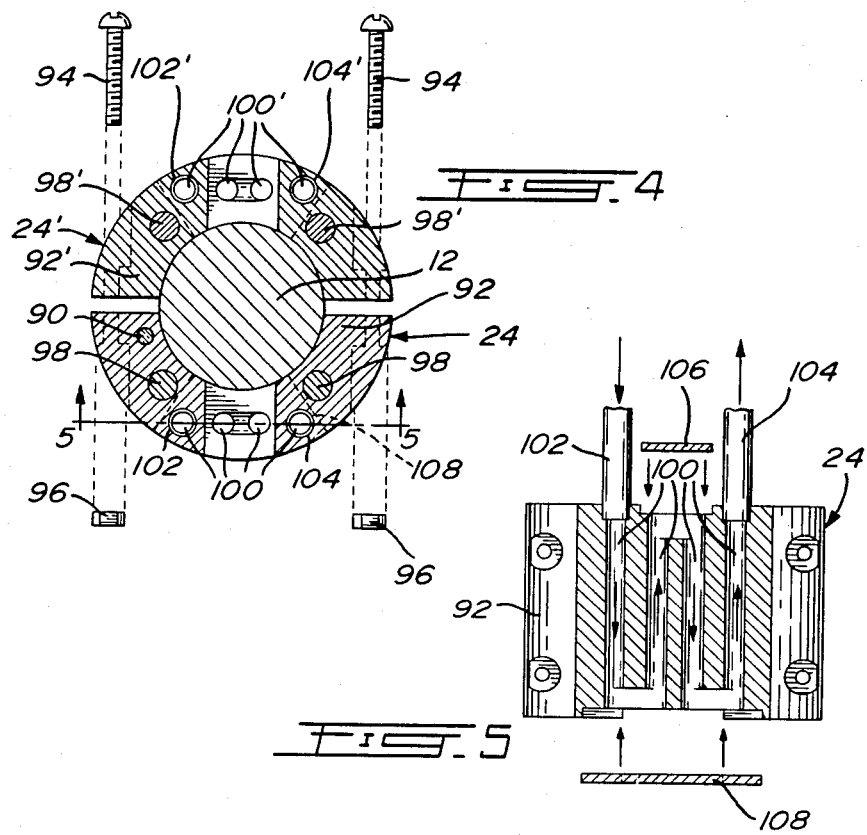
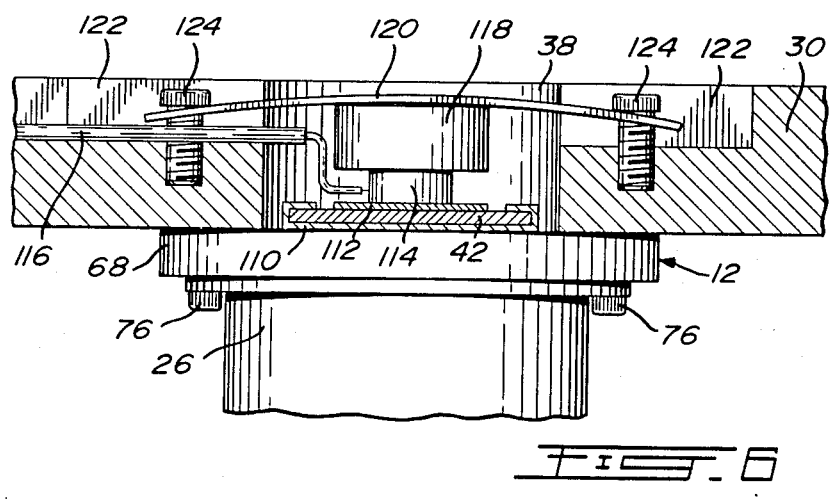

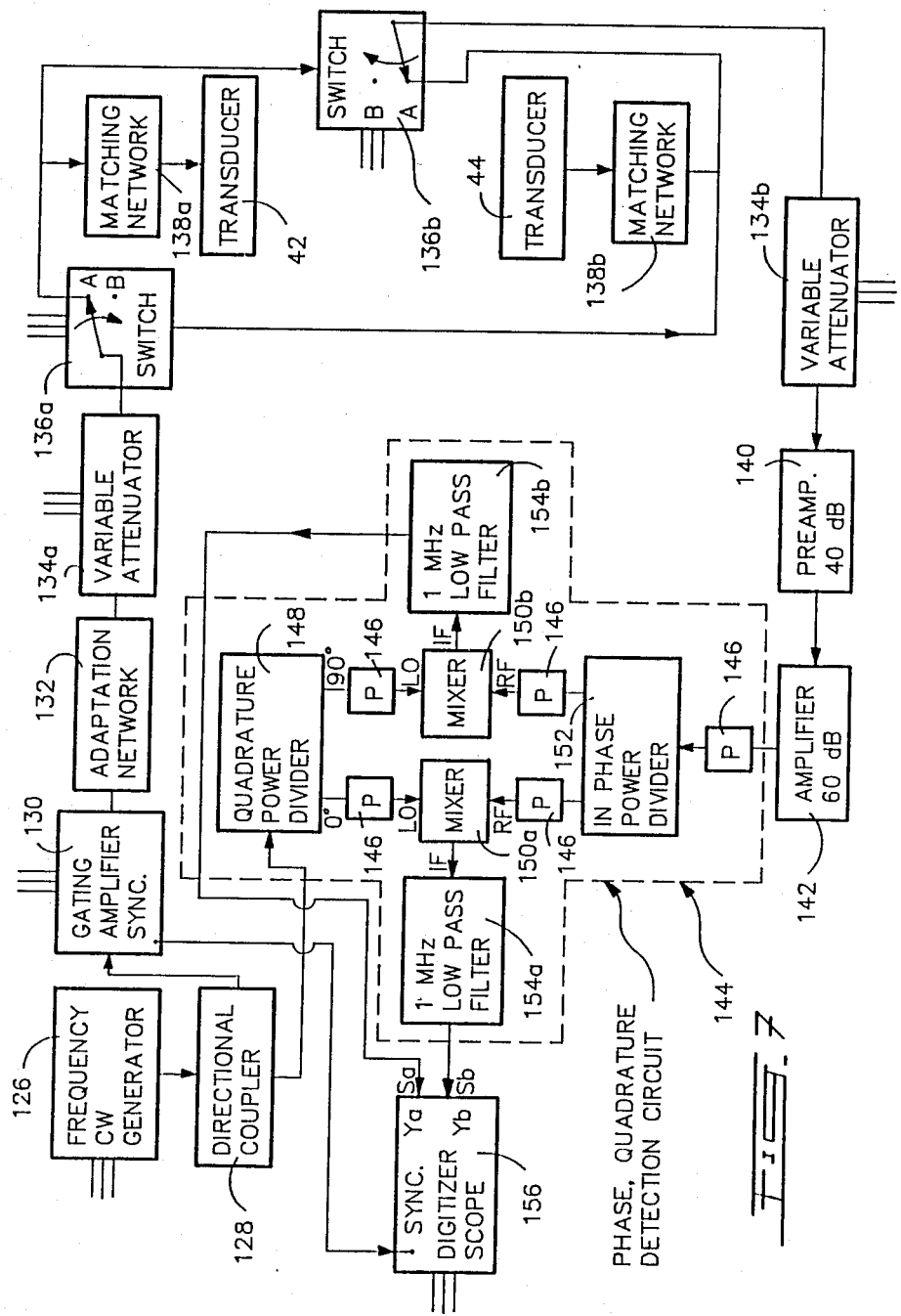

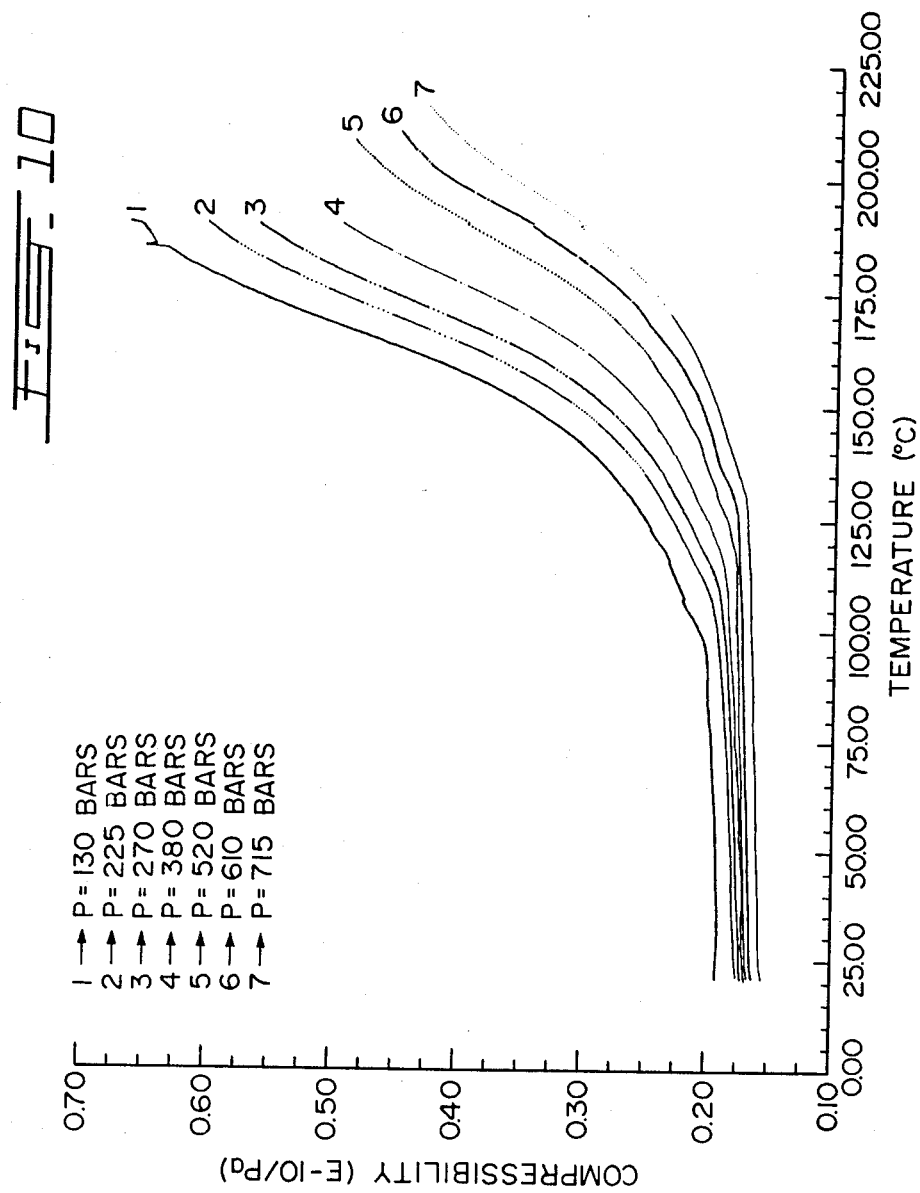

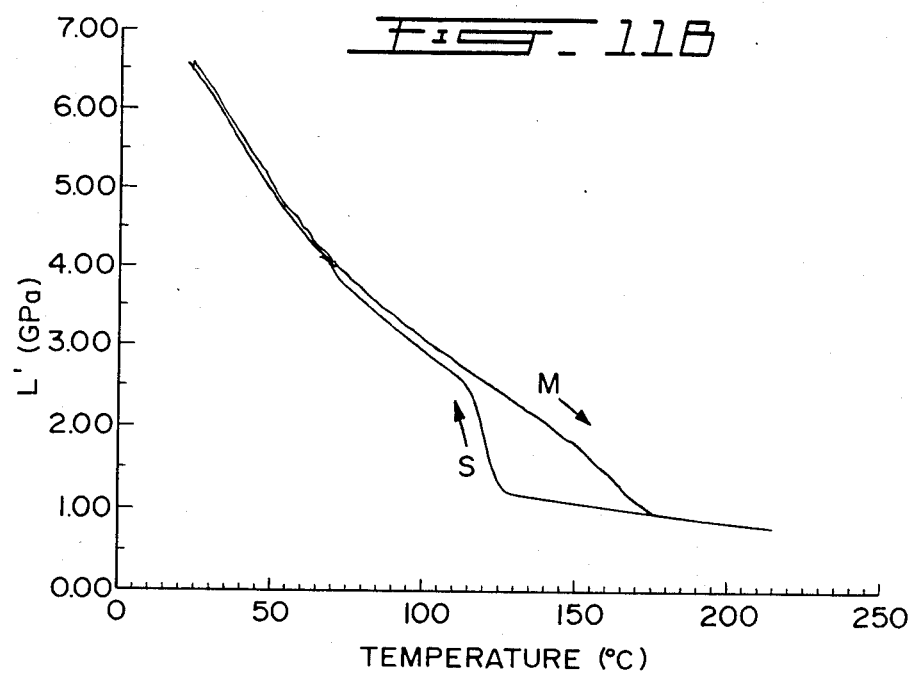
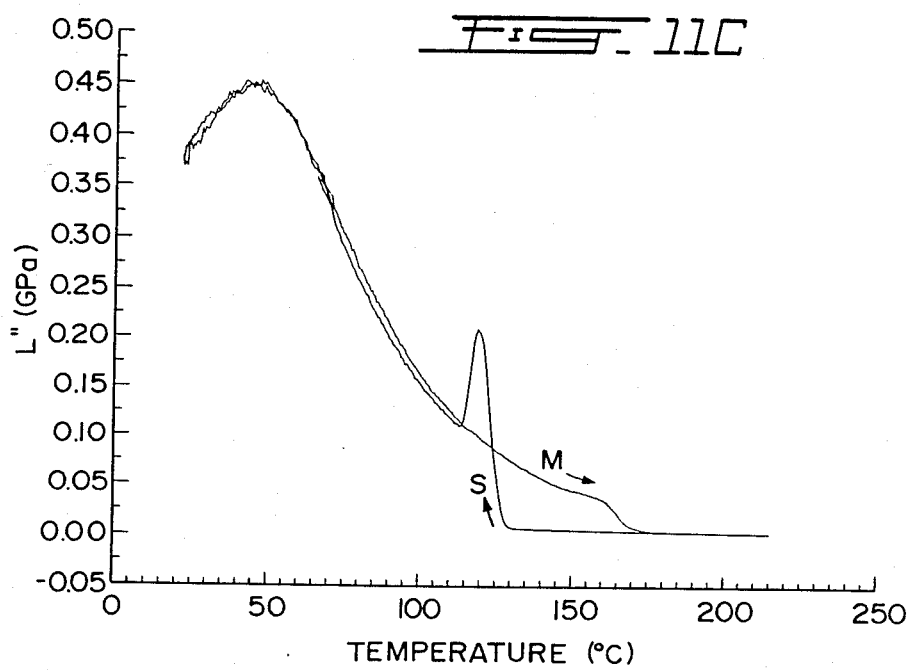

ULTRASONIC CHARACTERIZATION OF POLYMERS UNDER SIMULATED PROCESSING CONDITIONS

BACKGROUND OF THE INVENTION

The present invention relates to a method and apparatus for the ultrasonic characterization of polymers under simulated processing conditions. More particularly, the invention is directed to an improved buffer rod technique enabling the complete characterization of polymer materials at temperature and pressure conditions normally encountered in actual processing.

Processing of polymers includes heating, melting, applying pressure and cooling, all at certain rates under given conditions of flow geometry. The corresponding parameters (temperature, temperature gradient, pressure and time) will affect the flow properties during processing and thus influence the quality of the end product.

When considering polymer processing, it is important to distinguish between two classes of synthetic polymers: the thermosets and the thermoplastics. The thermosets are those where a crosslinking agent (hardener) is added to a low molecular weight liquid (resin); polymerization is carried out in a mold and yields a stable end product. The process is irreversible. The second class is that of thermoplastics, more commonly referred to as plastics; the term "plastics" comes from the fact that the resin material is heated until pliable and soft enough to be formed into the desired shape. In contrast to thermosets, thermoplastics are high molecular weight polymers which preserve their chemical and structural identity during processing.

Basically, polymers are constituted of molecules comprising a large number of repeating units which are covalently linked together to form chains. In turn, the attraction between the chains is provided by secondary bonds which, depending on the nature of the molecules, may be Van-der-Waals forces, dipole-dipole interactions, hydrogen bonds and, if crosslinking is present, covalent bonds. At the higher temperatures, typically 200°–300° C., the configuration for the chains is random, like that of a viscous liquid. The specific volume (V) of this liquid can be described as the sum of a free volume ($V_f$) associated with holes and packing irregularities, and that of an occupied volume ($V_o$) corresponding to the effective volume occupied by the molecules under Brownian agitation. As temperature (T) is lowered, the thermal excitation diminishes and this is accompanied by a decrease of the specific volume ($\alpha = d(\ln V)/dT \simeq 10^{-3}/\text{deg}$), mainly due to the decrease of free volume ($V_f$). This collapse of $V_f$ limits the freedom of movement for the chains, which results in the increase of viscosity ($\eta$). Upon approaching a certain characteristic temperature, referred to as the glass transition temperature (Tg), the free volume has so diminished that the possibility of conformational rearrangements of the chains has become strongly hindered. In this region of temperature, the response to a perturbation is characterized by a finite relaxation time, $\tau(10^3$ to $10^{-9}$ sec), so that material properties such as moduli and viscosity are also time and frequency dependent. The time or frequency dependent nature of material properties is a characteristic of polymers and is referred to as viscoelasticity. On going through Tg, the glass transition temperature, the thermal expansion suddenly drops ($\alpha \simeq 10^{-4}/\text{deg}$) and the viscosity increases to such values ($\eta \simeq 10^{13}$ poises) that the structure is frozen in, and the material appears as a solid. Now, because of its high viscosity, the liquid may be undercooled to various degrees so that the value for Tg is dependent on the cooling rate. Therefore, the structure and properties of the solid are contingent not only upon the nature of the molecules, but also, to a large extent, upon the thermal history near Tg, i.e., temperature, pressure and cooling rate.

According to their structure, solid polymers are found to be either amorphous or semi-crystalline. Amorphous polymers, such as the usual atactic polystyrene (PS) and polymethyl-metacrylate (PMMA or plexiglass), are characterized by the absence of long range ordering of the molecules. Semi-crystalline polymers, such as polypropylene (PP) and polyethylene (PE), are those where the formation of ordered regions (crystals) dispersed in the amorphous matrix is favoured by strong intermolecular forces and by the highly regular structure of the chains. In the case where such ordering exists, the semi-crystalline material still exhibits a glass transition temperature (Tg) which is related to the amorphous nature of the matrix, but also a melting point (Tm) and a solidification point (Ts) which are related to the crystalline phase.

Polymeric materials can be formed by a variety of fabrication techniques. The major component in most processing lines is the extruder. The raw polymer in pellet or powder form is fed from a hopper to a rotating screw. The material is driven through a cylinder where it is heated, compacted and softened. In the simple extrusion process, the screw forces the material through a die of a given shape and the shaped extrudate (tubing, pipe, fiber, sheet, insulating wire coatings . . . ) is then cooled to solidification. In blow molding, a tube is first extruded and while the material is still in the molten state, an air jet inflates the tube to the desired form, either inside a mold (blow molding) or as thin-wall oblong ballon (blow film extrusion). In injection molding, a charge of molten material is first accumulated in the nozzle of the extruder before it is injected in a cold mold. In rotational molding, a powder is placed into a cold mold and the mold is then rotated as it is heated; this causes the polymer to soften, melt and coat the inside of the mold to form a hollow object. Calendering of thermoplastics involves feeding the polymer between a series of heated rollers that flatten, extend and draw the compound into a sheet or film. In the thermoforming process, a thermoplastic sheet is first heated to its softening point, then shaped into a die by either a mechanical force, air pressure or vacuum. Compression molding (or transfer molding) is one where a press with heated platens is utilized to shape the material into a hot mold. The above methods are those which are typically used for thermoplastics; however, in many cases, they can also be used for processing thermosets, e.g., injection molding, rotational molding and compressional molding.

From what has been said above about the nature of the polymer material and its processing, it can be foreseen that the incentive for methods of testing both the end use product and the raw material is very strong. Indeed, a number of analytical techniques have been developed which can be classified as either reliability or thermostructural tests. Reliability tests are made under conditions that approximate the end use environment and serve to predict long term stability; such tests include time dependence of compliance, creep, time to rupture, brittleness, hardness, resistance to abrasion, wear, friction, and fatigue, electrical resistivity and strength.

The characterization of the raw material, on the other hand, is made with the help of thermostructural tests which aim at correlating structural changes that occur within the polymer wich changes in a thermodynamic property; they include specific heat, thermal conductivity and expansion, degradation, static and dynamic mechanical analysis, dielectric behaviour, I.R., Raman and N.M.R. spectroscopy.

For a given application, one technique may prove to be more adequate, but none is universal. Moreover, the above mentioned techniques are often difficult to implement and are time consuming; also, they involve delicate and costly instrumentation and require skilled technicians. Therefore, quality control laboratories often rely on tests which have been elaborated on common sense basis, such as melt flow index, capillary flow and softening point index. Such tests are often very useful but they usually involve a combination of a great number of physical parameters which makes them difficult to interpret in terms of more fundamental and basic material properties. As a consequence, the results obtained from such tests are specific to the test conditions and cannot be extrapolated to different conditions; the results are indicative and not quantitative.

As previously mentioned, in the course of being processed, the polymer material is subjected to a number of different thermomechanical conditions which involve temperature, pressure and time. Given that the properties of the final end use material are highly dependent upon its past thermal history, it would be highly desirable to have means of characterizing the raw polymer under conditions that are representative of those which it will encounter during the processing operations, giving access to the fundamental material properties.

In this perspective, ultrasonic methods for the testing of polymers have been developed using either liquid immersion techniques, solid buffer rod techniques and direct contact techniques.

Ultrasonic immersion techniques are rather well known, whereby a sample is placed in the path of a sound beam between a transmitting transducer and an opposite receiving transducer which are immersed in a sound conducting fluid. Changing the orientation of the sample with respect to the sound path allows, under certain conditions, to generate longitudinal waves (when the sound beam is perpendicular to the plane of the sample) or shear waves (when the angle of incidence exceeds a critical value for total internal reflection, according to Snell's law). A method has been described in H. A. Waterman, Kolloid-Zeitscrift and Zeitschrift Fur Polymere, 192,1 (1963) that allows measurements to be made on solid materials only. The method precludes testing of polymers at higher temperatures because the material may be deformed. The approach was modified as shown in U.S. Pat. No. 3,858,437 to Jarzynski et al. and in the article by B. Hartmann and J. Jarzynski, *J. Acoust. Soc. Am.* 56, 1469 (1974), whereby the sample is held stationary in a horizontal position and the transducer assembly itself is rotated around the sample. In this technique, experiments must be carried out on a number of specimens of different thicknesses such that the method is restricted to temperatures where the attenuation is not so high as to prohibit the transmission of sound through the thicker samples.

U.S. Pat. No. 4,346,599 to McLaughlin et al. and the article by G. W. Paddison, *Proc. IEEE Ultrasonics Symposium*, 502 (1979) describe an improved version of the technique. In particular, the authors of these references point out to the necessity of measuring the thickness (1) and the density ($\rho$) or specific volume ($V = 1/\rho$) at each of the temperatures at which acoustic measurements are made. The authors rightfully point out that polymers have a mass density with a temperature dependence which is important and must be accounted for in the determination of the storage and loss moduli. Furthermore, the authors call attention to the fact that the density of polymers may depend on the rate of heating.

In its application to studies on polymers, the immersion technique, however sophisticated, suffers some inherent limitations with respect to temperature and pressure. In order for a given method to be versatile, it should allow measurements to be performed in as broad a temperature range as possible, while the immersion technique allows to cover only a limited zone below the boiling point of the sound transmitting liquid where the viscosity of the liquid is still reasonably small. Also, the properties of polymers being strongly temperature dependent, an accurate measurement of temperature is required, which is difficult to obtain with the immersion method; unless care is taken to stabilize the temperature of the liquid, thermal gradients will exist which will perturbate the temperature of the sample. Also, the properties of polymers are influenced by the rate of temperature change. In order to permit the study of these effects, the technique should allow a close control of heating or cooling rates over as broad a range as possible. This is not possible using an immersion apparatus, given its high thermal inertia (transducer assembly, immersion fluid, etc.). Another important restriction stems from the fact that the immersion liquid will very often chemically react with the polymer, especially at high temperatures, and this will invalidate all results. Finally, during processing, the molten polymer will also experience very dramatic pressure changes (0–2 KBars) and an experimental method is required which allows to study the influence of pressure; the immersion technique cannot be easily adapted to studies under such conditions.

The immersion technique also suffers from some technical drawbacks. As can be seen in U.S. Pat. No. 4,346,599, the apparatus requires a great number of mechanical and moving parts (e.g. motors, gears, chains, cams, etc.) which demand minute adjustments. Furthermore, mechanical tunings must be made before any measurement (e.g. align sample, rotate transducers and find normal incidence conditions, rotate sample and find critical angle for extinction). Such tunings are critical and could lead to erroneous results if not performed properly. As such they constitute a source of measurement error. Also, they must be performed manually by an operator and because of this, the immersion technique cannot be made fully automatic.

Ultrasonic methods using solid buffer rod techniques are known. In such techniques, the sample is placed between two solid (metal or glass) rods. A first transducer acting as a transmitter is attached to the free end of one rod and a second transducer, the receiver, is attached to the free end of the other rod. The transmitter produces a burst of ultrasound which travels through the first rod, part of the energy being transmitted through the sample where it interacts with the material. Then, the ultrasound impinges on the second buffer rod and part of the energy is directed along the rod to the receiver where it is detected. Reference to such methods were made in the aforementioned McLaughlin et al. patent and can also be found in the review article by H. J. McSkimin, "Ultrasonic Methods for Measuring the Mechanical Properties of Liquids and Solids" in "Physical Acoustics", edited by W. P. Mason, Academic Press, New York (1964), Vol. I-A, Chap. 4, pp. 271-334.

All of the aforementioned techniques suffer a common most important drawback in that none provide the simultaneous measurement of density ($\rho$) or specific volume ($V=1/\rho$). In the technique described by J. R. Asay, D. L. Lamberson and A. H. Guenther, *J. Appl. Phys.*, 40,4 (1969) and D. L. Lamberson, J. R. Asay and A. Guenther, *J. Appl. Phys.*, 43,3 (1972), the thickness of the polymer sample is estimated indirectly by use of an ad hoc calculation, which involves a great deal of uncertainty. In all the other techniques, a fixed length spacer is placed between the buffer rods, which determines the length of the sample. Under such conditions, either the sample is confined and cannot expand nor contract freely such that the pressure conditions are unknown, or the sample is allowed to leak out of the cavity such that its mass is unknown, which makes impossible the determination of density.

As previously stated, an experimentation carried out on polymer materials requires close control of thermal history (value of temperature, prescribed heating or cooling rates) over extended ranges. However, the above mentioned techniques are restricted to limited temperature ranges (usually between 20° and 100° C.) and furthermore make no provision to control the heating and/or cooling rates. Measurements are usually carried out either at fixed temperatures or at a heating or cooling rate which is determined by the thermal inertia of the apparatus. Moreover, none of these techniques are designed to allow measurements under varying and controlled pressure conditions.

The buffer rod technique is useful in the case where high attenuation in the material under investigation imposes the use of short samples. In such situations, the buffer rods serve to circumvent problems associated with reverberation of sound by providing a time delay. However, other methods are available whereby the transducers are directly bonded to the sample (direct contact techniques).

An application of the technique to measurements under pressure is described in Asay et al. and also in Lamberson et al. In this application, the transducer-sample assembly is contained in a high pressure vessel and immersed in a pressure transmitting fluid; a furnace, enclosed in the pressure vessel, allows to heat the sample. For utilization in studies on polymers, such a design suffers the same drawbacks as those mentioned above, concerning the immersion technique and others.

The first drawback comes from that the temperature is limited to within the range specified for the hydraulic fluid and pressure vessel. Secondly and most importantly, because of the high thermal inertia, the heating and cooling cannot be controlled and the apparatus is limited to measurements performed at preset values of temperature. Thirdly, there arises the possibility that the sample be degraded by the hydraulic fluid through chemical reaction. Finally, the technique is laborious to operate as it involves making new bonds between the transducer and the sample for each different sample; the instrument is not easy to implement as it involves a number of technical difficulties associated with leakage of the hydraulic fluid.

SUMMARY OF THE INVENTION

It is therefore an object of the invention to overcome the above drawbacks and to provide a method and apparatus for ultrasonically characterizing polymer materials while simultaneously monitoring the static behaviour of the polymer undergoing ultrasonic testing, with a view to providing both a thermodynamic and viscoelectric characterization of the polymer.

According to one aspect of the invention, there is thus provided a method of ultrasonically characterizing polymer materials, which comprises the steps of:

(a) holding a sample of a polymer in confinement between two axially aligned buffer rods having opposed parallel end surfaces spaced from one another to define a gap filled with the polymer sample, the polymer sample being acoustically coupled to the opposed end surfaces of the buffer rods;

(b) transmitting ultrasonic waves through one of the buffer rods in a direction toward the polymer sample for intereaction therewith;

(c) subjecting the polymer sample to controlled temperature or pressure variations over a predetermined period of time, the variation in temperature or pressure being effected via the buffer rods;

(d) continuously monitoring phase and amplitude variations of the ultrasonic waves having intereacted with the polymer sample the while simultaneously monitoring thickness variations of the polymer sample, over the predetermined period of time, to obtain data comprising phase, amplitude and thickness values measured as a function of temperature or pressure and time; and (e) processing the data obtained in step (d) to derive characteristic parameters providing both a thermodynamic and viscoelastic characterization of the polymer.

The invention also provides, in a further aspect thereof, an apparatus for carrying out a method as defined above. The apparatus of the invention comprises a pair of axially aligned buffer rods having opposed parallel end surfaces spaced from one another to define a gap for receiving a sample of a polymer, and sample holding means for holding the polymer sample in confinement between the buffer rods while allowing compression or expansion of the polymer sample through axial displacement of the rods toward or away from one another, the polymer sample being acoustically coupled to the opposed end surfaces of the buffer rods. Rod alignment maintaining means are provided for maintaining the buffer rods in alignment with one another while allowing relative axial displacement thereof, the rod alignment means including means allowing transmission of pressure through the rods to the polymer sample for subjecting the sample to controlled pressure variations. Temperature control means including constant temperature heat sink means thermally anchored with the buffer rods are also provided for subjecting the polymer sample to controlled pressure variations.

The apparatus of the invention further includes ultrasonic transducer means acoustically coupled with one of the buffer rods for transmitting therethrough ultrasonic waves in a direction toward the polymer sample for intereaction therewith; first monitoring means for continuously monitoring phase and amplitude variations of the ultrasonic waves having intereacted with the polymer sample, over a predetermined period of time during which the polymer sample is subjected to the controlled temperature or pressure variations, to provide data comprising phase and amplitude values measured as a function of temperature or pressure and time; second monitoring means for simultaneously monitoring thickness variations of the polymer sample, over said predetermined period of time, to provide data comprising thickness values measured as a function of temperature or pressure and time; and data processing means operatively connected to the first and second monitoring means for processing the data to derive characteristic parameters providing both thermodynamic and viscoelastic characterization of the polymer.

The method and apparatus according to the invention can be used for testing both thermosets and thermoplastics, including liquids and solids, pure resins, blends and composite materials. From the measured phase and amplitude, sample thickness and weight, characteristic parameters such as density, specific volume, acoustic velocity and attenuation, storage and loss moduli can be accurately determined. The storage and loss moduli together with the specific volume may then be plotted as a function of different temperatures and pressures in order to characterize the properties of the polymer and establish a correlation between the static behaviour given by the specific volume and the dynamic properties given by the storage and loss moduli.

Based on such a characterization, one can thus more adequately control the polymer processing conditions, with a view to optimizing the properties of a given polymer for a given application.

BRIEF DESCRIPTION OF THE DRAWINGS

Further features and advantages of the invention will become more rapidly apparent from the following description of preferred embodiments as illustrated by way of example in the accompanying drawings, in which:

FIGS. 2A and 2B are elevation views of the buffer rods with their respective heat sinks seen removed;

FIG. 3A is a fragmentary sectional view illustrating the sample holder;

FIG. 3B is an enlarged sectional view of a detail shown encercled in FIG. 3A;

FIG. 4 is a sectional view taken along line 4—4 of FIG. 1;

FIG. 5 is a sectional view taken along line 5—5 of FIG. 4;

FIG. 6 is a fragmentary sectional view illustrating how the transmitting or receiving transducer is mounted to a buffer rod;

FIG. 7 is a schematic diagram of the electronic radio frequency circuit used for the generation and detection of ultrasonic waves;

FIG. 10 is a plot showing the thermal variation of the dynamic compressibility at different pressures;

FIG. 11B is a plot showing the thermal variation of the storage modulus on heating and cooling; and FIG. 11C is a plot showing the thermal variation of the loss modulus on heating and cooling.

DESCRIPTION OF PREFERRED EMBODIMENTS

Figure 1:
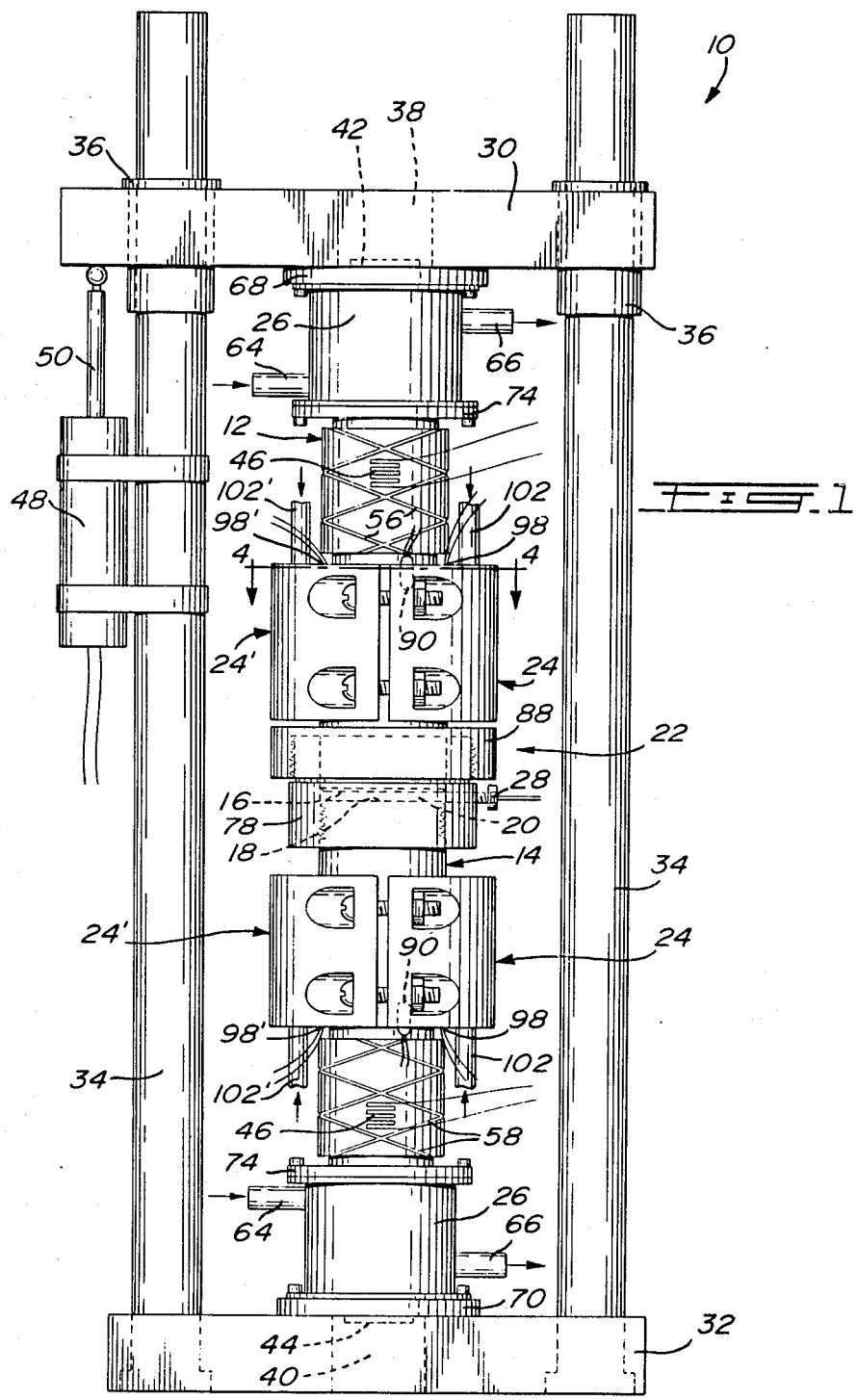
FIG. 1 is an elevation view of an apparatus according to the invention, for ultrasonically characterizing polymer materials.

Referring first to FIG. 1, there is illustrated an apparatus generally designated by reference numeral 10, for ultrasonically characterizing polymers. As shown, the apparatus 10 comprises two axially aligned buffer rods 12 and 14 having opposed parallel end surfaces 16 and 18 spaced from one another to define a gap which is filled with the polymer sample 20 under investigation. A sample holder 22 is screwed to buffer rod 14 and serves to hold the polymer sample 20 in confinement between the buffer rods 12 and 14, while allowing compression or expansion of the polymer sample through axial displacement of rod 12 toward or away from rod 14. Each buffer rod is provided with a pair of heating-/cooling devices 24 and 24' as well as with a heat sink 26 for subjecting the polymer sample 20 to controlled temperature variations, the temperature of the polymer sample being measured by means of a temperature sensing device 28 which is inserted in the sample holder 22.

In order to maintain the buffer rods 12 and 14 in axial alignment with one another while allowing relative axial displacement thereof, these are respectively secured to square plates 30 and 32 centrally thereof and at each corner of which is mounted a guiding column 34, the plate 32 being fixed and receiving in press-fit engagement the lower ends of the columns 34. The plate 30, on the other hand, is formed adjacent each corner thereof with a hole fitted with a bushing 36 and receiving therethrough a guiding column 34 in slidable engagement such the plate 30 together with the buffer rod 12 are freely movable along the guiding columns 34. The plates 30 and 32 are provided with central holes 38 and 40 giving access to ultrasonic transducers 42 and 44 which are acoustically coupled with the buffer rods 12 and 14. The transducer 42 acts as a transmitting transducer for transmitting ultrasonic waves through the buffer rods 12,14 and the polymer sample 20 held therebetween whereas the transducer 44 acts as a receiving transducer for receiving the ultrasonic waves transmitted through the polymer sample, when phase and amplitude monitoring is effected in transmission mode. In reflection mode, however, the transducer 42 acts as both a transmitting and receiving transducer.

The material selected for the construction of the plates 30,32 and guiding columns 34 was AISI 4130 steel alloy which usually enters the fabrication of dies.

The choice of material for the construction of the buffer rods 12 and 14 is more critical. The rods must be able to sustain extreme high and low temperatures, large thermal gradients and high level of stresses with negligible deformation and minimum dimensions. At the same time, the material should be adequate for ultrasonic propagation: namely, (a) the acoustic impedance (Z)—defined by $Z=\rho \cdot c$ where $\rho$ is the density and c the velocity of sound—should be small if possible, and (b) the material should have minimum attenuation for ultrasonic waves.

It was found that the materials which have the above suitable characteristics are titanium, stainless-steel and high-stress-proof steel. The construction described herein was made with high-stress-proof steel, but the same design characteristics also pertain to titanium and titanium based alloys and stainless steels.

The apparatus 10 is designed to fit between the platens of a laboratory type hydraulic press. The press is actuated by means of a hydraulic system of a commercial type which inclues high pressure impellers. Actuation of the press depresses plate 30 and buffer rod 12 and thus transmits pressure to the sample 20.

The pressure which is applied to the polymer sample 20 is measured by means of strain gauges 46 attached to the buffer rods 12 and 14. The strain gauges 46 are connected to a high sensitivity AC wheatstone bridge (not shown), the output of which is digitized by an analog/digital converter (not shown). The signal is fed to a computer (not shown) as data which in turn is used to control the pressure applied to the sample. Typically, the pressure on the sample 20 can be measured with an accuracy of ±0.5 bars and controlled to ±5 bars in the range of from 1 to 2000 bars.

Provision is also made to measure the thickness of the polymer sample 20 while being subjected to ultrasonic testing, under varying temperature and/or pressure conditions. To this end, the apparatus 10 is equipped with a linear-voltage-differential-transformer (or LVDT) 48 which is attached to a guiding column 34 and includes a probe element 50 movable with the plate 30 for sensing the position thereof. The LVDT 48 produces an electrical signal representing the displacement of the plate 30 in response to a compression or expansion of the sample 20; this signal is digitized by an analog/digital converter (not shown) and fed to the computer as data. By performing a first reading in the absence of sample and a second reading with the sample 20 in place in the sample holder 22, the thickness of the sample is deduced by subtraction of both readings. The thickness of the sample can thus be measured with an accuracy of ±5 μm, at all temperatures and pressures.

FIGS. 2A and 2B illustrate in more detail the buffer rods 12 and 14. The design of the buffer rods, i.e. material selection, length and diameter, is such that pressures up to 2000 bars can be transmitted to the polymer sample without noticeable deformation, wraping or buckling of the apparatus 10, in a range of temperatures extending from about −150° C. to about 400° C.

The buffer rods 12 and 14 are made identical with the exception that the bottom end of buffer rod 12 has a levelled edge 52 while the top end of buffer rod 14 is formed with threads 54, in order to accomodate the sample holder 22. They are designed such the polymer sample can be heated or cooled from both ends by two isothermic surfaces corresponding to the bottom end surface 16 of buffer rod 12 and the top end surface 18 of buffer rod 14. As such the heat transfer efficiency is optimized and the possibility for thermal gradients to exist is minimized. The design is such that the polymer sample can be subjected to temperatures from −150° C. to 400° C. without noticeable degradation of normal operational characteristics of the apparatus. The design is also such that the heating/cooling rate can be controlled from 0 to 1° C./sec in the temperature range of −150° C. to 400° C. with an accuracy of 1%.

Longitudinal and/or shear ultrasonic waves can transmitted efficiently in the frequency range from 0.5 to 20 MHz from the transmitting transducer 42 along the buffer rod 12, through the polymer sample 20, along buffer rod 14 and to the receiving transducer 44, in the pressure range from 1 to 2000 bars and temperature range from −150° to 400° C., providing the attenuation of the sample does not exceed 150 dB. In the case of more highly attenuating materials, the velocity and attenuation coefficients can determined using the reflection mode as will be described hereinbelow.

To this end, the end surfaces 16 and 18 of the buffer rods 12 and 14 must be flat and parallel to each other. It is also required that in attaching to plates 30 and 32, the buffer rods be well aligned and that the displacement of plate 30 does not disturb this alignment.

Moreover, the buffer rods 12 and 14 are designed such as to minimize the effects caused by beam diffraction and side wall effects. Indeed, a sound beam produced by a source of finite dimension, such as transducer 42, propagates with an increasingly larger diameter. This effect is referred to as beam diffraction. Thus, in propagating in the buffer rods 12 and 14, diffraction causes the sound to interact with the side wall and be reflected. Such reflections conjugate their effects and mix with the main beam giving rise to unwanted spurious signals. In the present invention, the unwanted effects of sound diffraction are eliminated by providing V-shaped grooves 56 and 58 on a surface portion of the buffer rods 12 and 14. As shown, the pattern is that of a double helix, one winding, the other unwinding. With this geometry, the reflection pattern is incommensurate and has little influence on the main beam. As a result, the spurious signals are reduced by more than 80 dB and cannot be distinguished from the electronic noise.

As shown in FIG. 2A, the buffer rod 12 is formed adjacent its upper end with a series of annular grooves 60 which are interconnected by axial grooves 60' arranged diametrically opposite one another. The buffer rod 14 is similarly formed adjacent its lower end with a series of annular grooves 62 interconnected by axial grooves 62', as shown in FIG. 2B. These grooves are adapted to receive thereover a heat sink 26 in the form of a sleeve having inlet and outlet ports 64 and 66 for circulation of cooling water. The arrangement is such as to form inside the heat sink 26 a circumferential channel through which the cooling water is circulated for maintaining the ends of the buffer rods at a constant temperature. The heat sinks 26 are sealingly connected to the upper and lower flanges 68 and 70 of buffer rods 12 and 14 by means of suitable sealing elements 72, collar members 74 and screws 76. They serve the dual purpose of (a) providing a constant temperature heat sink required for an adequate control of temperature and (b) ensuring that the transducers 42 and 44 and the transducer/buffer rod bond are maintained at a constant temperature.

Turning to FIGS. 3A and 3B, the sample holder 22 serves the main purpose of confining the polymer sample 20 in the gap between the buffer rods 12 and 14, at all values of temperature and pressure, whether the sample is solid or liquid. As shown, the sample holder 22 comprises a thick wall cylinder which constitutes the main body 78. The body 78 has an inner surface portion which is threaded for engagement with the threaded end of buffer rod 14, and is formed with an inwardly protruding rib 80 which provides seating for a compression ring 82. The upper part of the main body 78 is recessed to receive a sealing ring 84 having a U-shaped cross-section. The sample holder 22 is completed by a seal retaining piece 86 and a threaded cover 88. After assembly, the sample holder is screwed on the threaded end of buffer rod 14 and tightened by hand. The sample in the form of a preshaped disc, or in any other form (powder, pellets, liquid) is placed inside and buffer rod 12 is then inserted. The final sample is shaped in situ as a disc from 1.5 to 10 mm in thickness, by compression molding.

In operation, the sample holder 22 as designed prevents liquid polymer from leaking outside the gap. Upon application of pressure, the buffer rod 12 exerts a vertical force on the main body 78 which comes to rest on the threads; the compression ring 82 is made of a soft material such as teflon, copper or aluminum and while compensating for the play in the threads produces a leak tight seal. On the other hand, a minute quantity of liquid polymer climbs between the wall of the main body 78 and buffer rod 12 and fills the U-shaped ring 84. As pressure is further increased, the liquid forces open the U-shaped ring 84 which then rests on the shoulder of the main body 78, on the surface of buffer rod 12, and is pushed against the retaining piece 86. As shown in FIG. 3B, the forces are equilibrated inside the ring 84 which then provides a leak tight seal at all pressures.

The sample holder 22 is easily removed and allows the sample to be retrieved. The disc can then be weighed. With the value obtained for the mass (m), together with the known value for the inner diameter (d) of the sample holder 22, the specific volume (V) or density ($\rho = 1/V$) can thus be determined at all temperatures and pressures through measurement of the sample thickness (1).

The arrangement therefore allows to obtain values for the thickness (1) and the specific volume (V) or mass density ($\rho$) in situ and on the same sample as that on which ultrasonic measurements are performed.

In addition to the temperature sensing 28 which is inserted in the sample holder 22, two further temperature sensing devices 90 are provided, which are inserted in the heating/cooling devices 24, as shown in FIG. 1. The temperature sensing devices 28 and 90 may consist of thermocouple or resistance temperature devices.

The structure of the heating/cooling devices 24 and 24' is illustrated in more detail in FIGS. 4 and 5. As shown, the devices 24 and 24' are in the form of two semi-cylindrical members 92 and 92' made of brass, which are clamped tight around the buffer rod 12 (or 14) with screws 94 and nuts 96. The member 92 is formed with two axial holes each of which accepts a tightly fitting heating cartridge 98. The member 92 is also provided with four additional holes 100 which are interconnected to form a continous channel between inlet and outlet tubings 102 and 104, in which a cooling fluid such a liquid nitrogen can be circulated for cooling purposes. The two holes 100 between the inlet and outlet tubings 102 and 104 are sealed by a sealing plate 106 whereas all four holes 100 are sealed at their other end by a further sealing plate 108. The member 92' is similarly provided with two heating cartridges 98' and four axial holes 100' with inlet and outlet tubings 102' and 104' for circulation of cooling fluid. When installed on a buffer rod, the heating/cooling devices 24 and 24' are preferably wrapped with a thermal insulating material to minimize heat leakage to the surroundings.

The design of the heating/cooling devices 24 and 24', e.g. the choice of brass as high conductivity high thermal inertia material, the axial geometry, diameter(s) and length(s), is made to satisfy the temperature control requirements previously mentioned. In particular, the heating/cooling devices are such that the flow of heat is perpendicular to the end surfaces 16 and 18 of the buffer rods 12 and 14 which are in contact with the polymer sample 20. This ensures that the sample 20 is heated (or cooled) from an isothermal environment with which it is in good thermal contact through the clamping force of the buffer rod 12.

The heating cartridges 98 and 98' are connected to a solid state temperature regulator (not shown) which in turn is controlled by the computer. The cooling circuit, on the other hand, is connected to a solenoid operated system of valves (not shown) which under computer control allow the flow of an adequate cooling fluid.

The measurement of temperature is preformed through the temperature sensing devices 28 and 90. The voltage signal of each of these temperature sensing devices are digitized by an analog/digital converter (not shown) and sent to the computer as data. The data of device 28 is recorded as being the actual temperature (T). The data of devices 90 are used as feedback signals to the solid state temperature regulator for the control of temperature (T) and heating/cooling rates (dT/dt).

One of the features of the present invention is that it allows one to study the propagation of both longitudinal and shear ultrasonic waves through the polymer sample 20 in the frequency range from 0.5 to 20 MHz.

The propagation and detection of the ultrasonic waves is accomplished through the use of two transducers; one acting as a transmitting transducer 42 is mounted on the top end of buffer rod 12 and the other acting as a receiving transducer 44 is attached to the bottom of buffer rod 14.

As shown in FIG. 6, the transducer 42 which consists of a piezoelectric plate is provided on one side with a ground electrode 110 and, on the other side, with a center or active electrode 112. The transducer assembly is bonded to the surface of the buffer rod 12 through the access provided by the hole 38 located at the center of the plate 30. A brass electrode 114 soldered to the center conductor of a coaxial line 116 leading to or from the radio frequency circuit (shown in FIG. 7) is placed on the transducer's center electrode 112, and topped by an insulating disc 118. The insulating disc 118 is maintained in place by a leaf spring 120 which extends through a rectangular groove 122 intersecting the hole 38 and is loaded by screws 124. The assembly is sturdy, reliable and practical; it allows to change the transducer 42 easily.

The receiving transducer 44 is attached to the bottom of buffer rod 14 in exactly the same manner.

For the present application, transducers made of material such as ceramics, quartz and lithium niobate (LiNb) are found to have adequate efficiency for either longitudinal or shear wave operation. While a number of transducer/bond combinations are possible and give satisfactory results, three specific arrangements are particularly useful and interesting.

In a first option, longitudinal and shear wave experiments are carried out independently with different appropriate transducers. For longitudinal waves, a Y-cut lithium niobate crystal is found to be very efficient. In this case, a liquid such as silicone oil produces an adequate acoustic bond between the transducer and the buffer rod. For shear waves, a Y-cut quartz crystal was found to yield pure mode signals with little perturbation from spurious modes. In this case, a solid bond is required. Salol produces a good quality bond that is reliable and can be easily reproduced; Salol also allows for easy installation and removal of the transducers.

According to a second option, an X-cut lithium niobate transucer is used with a solid bond such as Salol. With this arrangement, both longitudinal and shear waves are produced with the same transducer. In this case, the efficiency with regards to longitudinal waves is not as good as in the first option, using a Y-cut LiNb crystal, but is quite adequate. Since the propagation velocity for the longitudinal wave is much greater than that for the shear wave, and since the path length is long, between the transmitting transducer 42 and the receiving transducer 44, at the time they are detected by the receiving transducer 44, the signals corresponding to each mode are well separated in time (50 μs) and can be easily identified and selected by an appropriate electronic gating or timing device. Thus, with this option, experiments on the propagation of both longitudinal and shear waves can be performed in the same run, without changing the transducer.

In the third option, a Y-cut quartz transducer with a non overlapping groung electrode is placed on the buffer rod with a hard bond such as Salol. This transducer serves to produce shear waves. A second X-cut quartz (longitudinal mode) transducer with an overlapping bottom electrode is placed on top of the first using a liquid bond, such as silicone oil. This arrangement allows for a more efficient generation of the longitudinal mode than is obtained through the second option (using an X-cut lithium niobate crystal), but with some noticeable degradation in spectral purity. Also, the third option is more delicate to implement than the second option.

For the present application, resonant transducers are used which are polished and lapped for overtone operation. With this a transducer having a resonant frequency (fo) can be used at frequencies corresponding to odd number harmonics, such that $f=f_o(2n+1)$: $f_1=3f_o$, $f_2=5f_o$. . . . However, the efficiency diminishes at the higher harmonic numbers such that in practice a single transducer will be efficient up to the second harmonic ($f_2$). Therefore, a number (3 or 4) of transducers having different resonant frequencies are required to span the range from 0.5 to 20 MHz.

One important aspect of the invention concerns the coupling of ultrasonic waves into the polymer sample 20. The present technique allows for a number of ways by which good quality bonding can be obtained easily. Good quality bonding refers to bonds that have optimum, reliable acoustic properties that can be reproduced such that the ultrasonic measurements can be adequately performed in the ranges of frequency, temperature and pressure that are accessible through the present technique.

The first method, which is the most straight forward, simply involves bringing the buffer rods 12 and 14 in contact with the sample and applying a certain amount of pressure. The actual value of pressure which is required is determined experimentally. In the case of liquids, including molten polymers, only a very small pressure (1 or 2 bars) is needed to produce an optimum quality coupling; of course, this concerns longitudinal waves only since shear waves do not propagate in liquids. In the case of soft, leathery or rubbery materials, including polymers at temperatures above the glass transition (Tg), still only a slight pressure (1 to 5 bars) will allow to couple both longitudinal and shear waves. In the case of hard materials, including glassy polymers at temperatures below Tg, a pressure of 1 to 5 bars suffices for the coupling of longitudinal waves, whereas higher pressures from 30 to 50 bars are required for the coupling of shear waves.

The other method requires the use of a bonding agent, together with the application of a minute pressure (1 to 2 bars). For longitudinal waves, a drop or two of a liquid such as silicone oil on the end of each buffer rod is sufficient to ensure a good coupling to all types of materials. For shear waves, the coupling is accomplished using a small amount of such substances as Nonaq stopcock grease, honey or Salol. In all cases, the application of pressure produces an even bond which is thin and of uniform thickness. Also, the application of pressure ensures the contact and guarantees the bond against failure even though bond cracking may occur due to differences in thermal expansion coefficients between the buffer rods, bond and sample materials. Since the amount of bonding agent is very small, any chemical reaction with the polymer sample is limited to the surface of the sample and thus does not affect the bulk properties.

The generation and detection of ultrasonic signals, including data acquisition, are automated and under computer control. In the design of the electronic circuit which is schematically illustrated in FIG. 7, provision is made to cope with the extreme large changes in both attenuation and velocity that are to be expected in polymers. This requires that the dynamic range be large. Provision is also made that while the dynamic range is large, the sensitivity is also high and not deteriorated.

In FIG. 7, the following symbols have the following meanings;

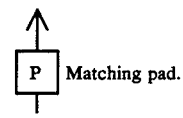

≡ Bus line to/from computer;

P   Matching pad.

As shown in FIG. 7, for the generation of ultrasonic waves, the signal from a computer controlled high frequency, high stability continuous wave (cw) generator 126 is fed to a directional coupler 128, the low amplitude output of which is sent to a computer controlled high power gated amplifier 130. Such amplifier produces high frequency pulses that are coherent and have a constant phase relation with the signal from the cw generators 126; the width of the pulses and their rate of repetition can be controlled. An adaptation network 132 provides the amplifier 130 with a constant load and prevents possible damage from reflected power. The high energy pulses are fed in a computer controlled variable attenuator 134a which is used to adjust the amplitude of the pulses. A computer controlled switch 136a directs the high frequency pulses either to transducer 42 or to transducer 44, via the matching network 138a or 138b. The networks 138a and 138b are used to match the electrical impedance of the transducers to that of the 50Ωcoaxial line 116 (FIG. 6) and to minimize the standing wave ratio. The matching networks 138a and 138b are also connected to a computer controlled switch 136b which is used to select the receiving transducer.

The signal from the selected receiving transducer is fed into a computer controlled attenuator 134b which is adjusted such that the output is kept within the linearity range of the following broad band preamplifier 140 and amplifier 142. The purpose of attenuators 134a and 134b is to allow full use of the available dynamic range of the system without having to modify the settings of either the power source 130, the matching networks 138a and 138b, or the amplifier 142. Such an arrangement ensures that the ultrasonic measurements are not perturbated by any changes in the characteristics of the electronic circuit, as would otherwise occur on changing the settings of instruments.

The phase and quadrature circuit 144 which is shown boxed in FIG. 7 is that which allows for the automated measurement of the ultrasonic phase and amplitude. Though the principle of operation for the circuit is simple, its implementation requires some care concerning impedance matching between the various physical components. For this, attenuating matching pads 146 are provided. The signal from the cw frequency generator 126 is fed to the directional coupler 128, the through coupled output of which is directed to a quadrature power divider 148. Such a device evenly distributes the incoming energy to two output ports, while introducing a 90° phase difference between each of the output signals. The output signals from the divider 148 are used as reference signals (0° reference and 90° reference) and each is fed to the local oscillator (LO) port of hybrid diode mixers 150a and 150. On the other hand, the output signal from amplifier 142 and which is to be analysed is fed into an in-phase power divider 152. Such a device evenly distributes the incoming signal between two parts; in this case, no phase shift is introduced between the output signals. Each divided output is fed in the radio frequency (RF) port of the diode mixers 150a and 150b. The mixers 150a and 150b are such that the signal at the RF port is combined to that of the LO port so that the output of the intermediate frequency port (IF) is equal to the square of the sum of the RF and LO signals. In the present design, the signals at the RF and the LO ports both have the same frequency, which is that of the cw generator 126, and differ only in phase and amplitude. Therefore, writing the reference signal as $K \sin(wt)$ and the unknown signal as $E \sin(wt+\phi)$, the IF output of mixer 150b is given by:

$$S_b = [K \sin(wt) + E \sin(wt + \phi)]^2$$

$$S_b = KE \cos\phi + \begin{bmatrix} \text{frequency dependent} \\ \text{higher order terms} \end{bmatrix}$$

Similarly, the IF output of mixer 150a is given by:

$$S_a = [K \sin(wt + \pi/2) + E \sin(wt + \phi)]^2$$

$$S_a = KE \sin\phi + \begin{bmatrix} \text{frequency dependent} \\ \text{higher order terms} \end{bmatrix}$$

These signals are respectively fed to low pass filters 154a and 154b which serve to eliminate the higher order terms. The resulting signals, $S_a = KE \sin\phi$ and $S_b = KE \cos\phi$, are simple DC pulses which differ through their amplitudes. The amplitude of each pulse is measured either on a digitizing oscilloscope or through a sample and hold system 156. A computer controlled gating/timing generator is used to select the signals to be analysed and the information concerning the amplitudes $S_a$ and $S_b$ is sent to the computer. The final analysis proceeds as follows:

$$\text{for the amplitude: } E = (1/K)(S_a^2 + S_b^2)^{\frac{1}{2}} \quad (1)$$

$$\text{for the phase: } \phi = \tan^{-1}(S_a/S_b) \quad (2)$$

In practice, changes in E are caused by changes in the ultrasonic attenuation of buffer rod 12/sample 20/buffer rod 14 assembly while changes in the phase $\phi$ are caused by changes in the sound transit time through buffer rod 12/sample 20/buffer rod 14.

The present design is simple and reliable. The dynamic range is of the order of 120 dB, with a sensitivity of ±0.1 dB on the amplitude and 0.5° on the phase.

All operations and measuring procedures are automated through a computer which is linked to the various components in a talk/listen mode as described above. Also, the various measurements are used to calculate the pertinent parameters, such as the storage and loss moduli, in a manner which is computer oriented.

The operation of the apparatus 10 is as follows.

The sample or specimen of the polymer material, in any shape or form (solid, liquid, bulk, powder or pellet) is inserted in the sample holder 22. The hydraulic system is activated and the sample 20 is compressed. The material is then heated until it is molten and the pressure is futher increased so that the sample is fully densified and the U-shaped ring 84 is filled with the molten polymer. It is then possible to either cool, remove and measure the mass (m) of the sample, or to proceed directly with the experiment and weigh the sample afterward. The information concerning the mass is entered in the computer, either the actual value for the mass (m) or the number 1.000, in which case the measurements and calculations yield relative results.

The information concerning the thermal history and pressure history under which the experimentation is to be carried out is entered in the computer. The control program is initiated and the apparatus is brought to the temperature and pressure conditions indicated for the start of the experiment. After equilibrium for the measured quantities—pressure (P), temperature (T), thickness (1), ultrasonic data $S_a$ and $S_b$ have been attained, initial starting values are recorded by the computer. The computer then initiates, runs and controls the experiment in the prescribed manner. Simultaneously, on a time sharing basis, the computer also acquires and stores the pertinent data concerning the pressure (P), temperature (T), thickness (1) and the ultrasonic signals $S_a$ and $S_b$. This control/measure cycle is performed in 9 to 10 seconds. Simultaneously, in a time sharing manner, the computer using the stored data performs the necessary calculations for the pertinent parameters such as density ($\rho$), specific volume (V), ultrasonic velocity (v) and attenuation (A). The results are illustrated on the computer's CTR screen and represented in a graphical form such that the values for V, v and A are plotted versus either temperature (T) or pressure (P) as specified by the computer operator. This calculation/display cycle is performed in 2 to 3 seconds such that a new computer routine is initiated every 11 to 13 seconds.

In order to calculate the ultrasonic velocity (v) and attenuation (A), it is first necessary to establish the equations that describe the propagation of sound, for both modes of operation which are accessible in this technique: the reflection mode and the transmission mode. From these equations, the manner of determining the velocity and attenuation of the ultrasonic waves, and the other parameters of interest such as the storage and loss moduli, compressibility and other is described in a way which is computer oriented. The manner of operating the computer to make these determinations will be apparent.

The transmitting transducer 42 (FIG. 1) produces a sound wave which travels in the buffer rod 12. Upon arrival at the buffer rod 12/ sample 20 interface, the amplitude of the wave is described by:

$$W_1 = W_0 \cdot \exp(-aL_3) \cdot \exp(jw)(t-L_3/c) \qquad (3)$$

where
Wo is the initial amplitude value
$w = 2\pi f$, and f is the frequency
$L_3$ is the length of the buffer rod 12
J is the imaginary number $\sqrt{-1}$
c is the velocity of sound in buffer rod 12
a is the attenuation of sound in buffer rod 12
t is the time.

The equation (3) is valid for both longitudinal and/or shear waves, provided a and c are chosen accordingly.

At the buffer rod 12/sample 20 interface, part of the ultrasonic energy is reflected and travels back to the transducer 42. This is described by a reflection coefficient R. Also, part of the energy is transmitted into the sample, the transmission coefficient being noted $T_S$; after it has traversed the sample, part of the energy is transmitted to buffer rod 14, here the transmission coefficient is noted $T_B$. The expressions for R, $T_S$ and $T_B$ are given by:

$$R = (Z_B - Z_S)/(Z_B + Z_S) \qquad (4)$$

$$T_S = 2Z_S/(Z_B + Z_S) \qquad (5)$$

$$T_B = 2Z_B/(Z_B + Z_S) \qquad (6)$$

where
$Z_B$ is the acoustic impedance for the buffer rod, and
$Z_S$ is the acoustic impedance for the sample.

The acoustic impedance which enters into equations (4), (5) and (6) is a complex quantity which in the case of a material M is given by:

$$Z_M = \rho_M c_M (1 + ja_M c_M/w) \qquad (7)$$

where
$\rho_M$ is the density of M
$c_M$ is the velocity of sound in M
$a_M$ the attenuation of sound in M
$w = 2\pi f$ and f is the frequency It is apparent from equation (7) which is a complex quantity that both R, $T_S$ and $T_B$ are also complex quantities.

In reflection mode, the same transducer such as 42 is used both for generating and receiving ultrasonic waves.

The measurement is performed, through proper adjustment of digitizer 156 synchronization, on that part of the wave which has been reflected at the buffer rod 12/sample 20 interface. On arrival at the transducer 42, the equation for the reflected signal is:

$$E_r = R \cdot W_0 \exp(-2aL_3) \exp(-2jwL_3/c) \exp(jwt) \qquad (8)$$

This equation represents a periodic wave of angular frequency $w = 2\pi f$ for which the amplitude is given by:

$$E = W_0 \text{mod}(R) \cdot W_0 \exp(-2aL_3) \qquad (9)$$

and the phase shift is given by:

$$\phi = \tan^{-1}[im(R)/re(R)] - 2wL_3/c \qquad (10)$$

where mod(R) represents the modulus of the complex reflection coefficient R, defined by Equations (4) and (7), and re(R) and im(R) are the real and imaginary components.

As was seen above (equations (1) and (2)), the experiment allows the amplitude E and phase $\phi$ to be measured directly. In actual operation, the quantities which are related either to the buffer rod such as density ($\rho_B$), length ($L_3$), velocity of sound (c) and attenuation (a) or to the electronic circuit, such as frequency (f), angular frequency ($w = 2\pi f$), gain factor (K) and initial amplitude (Wo) are known from performing a preliminary calibration measurement in the absence of a sample and stored in the computer memory. Equations (1), (2), (4), (7), (9) and (10) form a set of transcendental equations which are solved for v (the velocity) and A (the attenuation) in the sample by a computer iteration technique.

The reflection mode is useful and is to be preferred when the attenuation of ultrasound (A) in the sample 20 is so high as to prevent propagation across the sample length (1). Such is the case when performing shear wave measurements in a liquid-like material. However, in all other situations, the transmission mode is to be preferred. In the present technique, the transmission mode is selected when the attenuation (A) is less than 150 dB.

The transmission mode is to be preferred when the attenuation in the sample does not exceed 150 dB such that an ultrasonic wave can effectively be transmitted through the material. In the transmission mode, the signal which has traversed the full path from the transmitting transducer 42 to the receiving transducer 44 is measured. The equation which describes this signal is written as:

$$\begin{aligned}E_t = &T_B T_S W_0 \exp(-aL_3)\exp(-jwL_3/c) \\ &\exp(-Al)\exp(-jwl/v) \\ &\exp(-aL_4)\exp(-jwL_4/c)\exp(jwt)\end{aligned} \qquad (11)$$

In the present construction, the lengths of the buffer rods 12 and 14 have been made equal such that $L_3 = L_4$. Equation (11) can thus be written as:

$$E_t = T_B T_S W_0 \exp(-2aL_3) \exp(-Al) \exp(-j2wL_3/c) \exp(-jwl/v) \exp(jwt) \qquad (12)$$

Equation (12) is that of a periodic wave of angular frequency $w = 2\pi f$ having an amplitude given by:

$$E = \text{mod}(T_B \cdot T_S) \cdot W_0 \cdot \exp(-2aL_3) \exp(-Al) \qquad (13)$$

and a phase which is given by:

$$\phi = \tan^{-1}[im(T_B T_S)/re(T_B T_S)] - 2wL_3/c - wl/v \qquad (14)$$

where mod ($T_B T_S$) represents the modulus of the complex product $T_B T_S$, and re($T_B T_S$) and im($T_B T_S$) are the real and imaginary components.

As in the case of the reflection mode, the quantities E and $\phi$ are obtained directly from the measurements, through the use of equations (1) and (2). Here also, the ultrasonic velocity (v) and attenuation (A) for the sample are obtained by solving a set of transcendental equations which are given by equations (1), (2), (5), (6), (7), (13) and (14).

However, in the case where either a longitudinal or a shear wave can be transmitted through the sample, the following holds:

$$(a_M c_M / w) << 1$$

Then, equation (7) reduces to the real quantity:

$$Z_M = \rho_M c_M \quad (15)$$

As a consequence R, $T_S$ and $T_B$ are also real quantities. In particular, it can be noted from equations (4), (5) and (6) that:

$$T_B T_S = 4 Z_B Z_S / (Z_B + Z_S)^2 \quad (16)$$

Then, equation (13) for the amplitude reduces to:

$$E = T_B T_S W_0 \exp(-2aL_3) \exp(-Al) \quad (17)$$

which is used to calculate the attenuation (A). Also, equation (14) for the phase is reduced to:

$$\phi = -2wL_3/c - wl/v \quad (18)$$

which is used to calculate the velocity (v).

Thus, in the transmission mode, the equations which describe the propagation can be written and solved in a closed form. Such is not the case for the reflection mode where the full procedure must be used.

Listed hereinbelow are the different parameters that are of interest in studies on polymers and which can be measured through the present invention.

Specific Volume (V) and Density ($\beta = 1/V$)

As previously seen, the specific volume is obtained by monitoring the thickness (1) of the sample 20.

Linear Thermal Expansion ($\alpha$)

This coefficient is determined by calculating the relative slope (1/V) dV/dT obtained from monitoring the change of specific volume with temperature.

Static Compressibility ($\beta_S$) and Longitudinal Modulus ($L_S = 1/\beta_S$)

The compressibility, defined as $\beta_S = (-1/V) dV/dP$, and hence the longitudinal modulus $L_S = 1/\beta_S$ are obtained from the change of specific volume with pressure.

Dynamic Dilational (L) and Shear (G) Moduli

According to the McLaughlin patent and the publication of McSkimmin, the storage (L') and loss (L") components of the dynamic longitudinal modulus ($L = L' + jL"$) are obtained from measuring the velocity ($v_1$) and attenuation ($A_1$) of longitudinal ultrasonic waves. These are given by:

$$L' = \rho v_1^2 [(1 - F^2)/(1 + F^2)^2] \text{ and} \quad (19)$$

$$L'' = 2\rho v_1^2 [F/(1 + F^2)^2] \quad (20)$$

where $F = A_1 v_1 / w$.

If $F << 1$ (in practice $F < 0.01$), then:

$$L' \simeq \rho v_1^2 \quad (21)$$

$$L'' \simeq 2\rho A_1 v_1^3 / w \quad (22)$$

Similarly, the storage (G') and loss (G") components of the dynamic shear modulus ($G = G' + jG"$) are obtained from the velocity ($v_s$) and attenuation ($A_s$) of waves, and are given by:

$$G' = \rho v_s^2 [(1 - H^2)/(1 + H^2)^2] \text{ and} \quad (23)$$

$$G'' = 2\rho v_s^2 [H/(1 + H^2)^2] \quad (24)$$

where $H = A_s v_s / w$

If $H << 1$ (in practice $H < 0.01$), then:

$$G' \simeq \rho v_s^2 \quad (25)$$

$$G'' \simeq 2\rho A_s v_s^3 / w \quad (26)$$

Other parameters

Other parameters that can be directly calculated from L and G are the bulk modulus (K), the Young's modulus (Y) and the Poisson ratio ($\nu$). By using well known relationships, the storage (K') and loss components of the bulk modulus $K = K' + jK''$ are given by:

$$K' = L' - 4G'/3 \text{ and} \quad (27)$$

$$K'' = L'' - 4G''/3 \quad (28)$$

The storage Y' and loss Y" components of the dynamic Young's modulus $Y = Y' + jY''$ are given by:

$$Y' = 9K'G'/(3K' + G') \text{ and} \quad (29)$$

$$Y'' = 9K'G'/(3K' + G') \quad (30)$$

The storage component $\nu'$ of the Poisson ratio is given by:

$$\nu' = (3K' - 2G')/2(3K' + G') \quad (31)$$

and the loss component $\nu''$ of the Poisson ratio by:

$$\nu'' = [\tan(G''/G') - \tan(L''/L')]/2[(v_1/v_s) - (v_s/v_d)]^2 \quad (32)$$

ILLUSTRATIVE MEASUREMENTS

The results shown in FIGS. 8, 9 and 10 were obtained with the present technique on a sample of amorphous polystyrene (Dow Chemical Styron 850). The frequency of the ultrasonic waves was 2.5 MHz and the heating rate was 2° C./min.

Figure 8A:
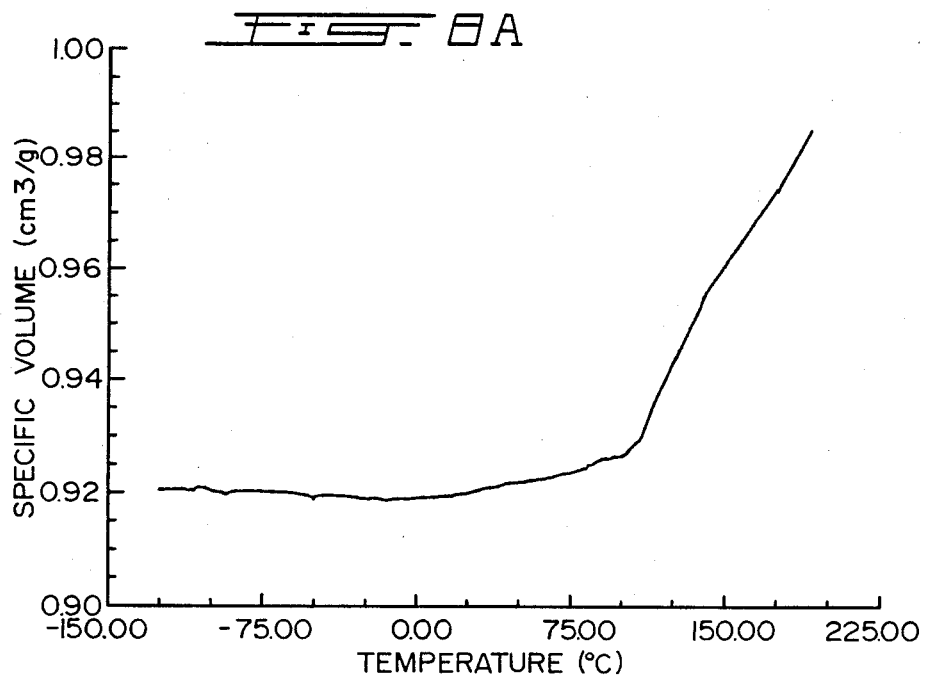
FIG. 8A is a plot of specific volume values against temperature, obtained from data provided by the apparatus shown in FIG. 1.

FIG. 8A shows the temperature variation of the specific volume V between −150° C. and +225° C. The knee which appears near 105° C. corresponds to the glass transition temperature Tg.

Figure 8B:
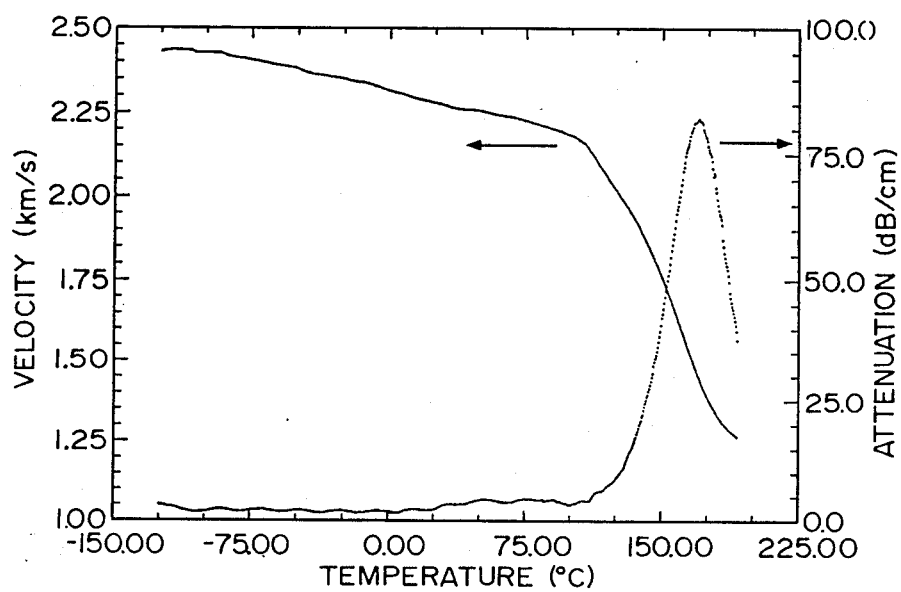
FIG. 8B is a plot of longitudinal velocity and attenuation values against temperature, also obtained from data provided by the apparatus of FIG. 1.

FIG. 8B shows the corresponding temperature variation for the longitudinal velocity $V_1$ and attenuation $A_1$. The knee that is observed in the velocity curve is seen to occur at the glass temperature Tg. Hence, the measurement of longitudinal velocity provides for a very accurate determination of Tg. The sharp maximum that is observed in the attenuation curve is representative of the well-known relaxation feature of the glass transistion phenomenon. The measurement of attenuation allows to describe the relaxation process.

Figure 8C:
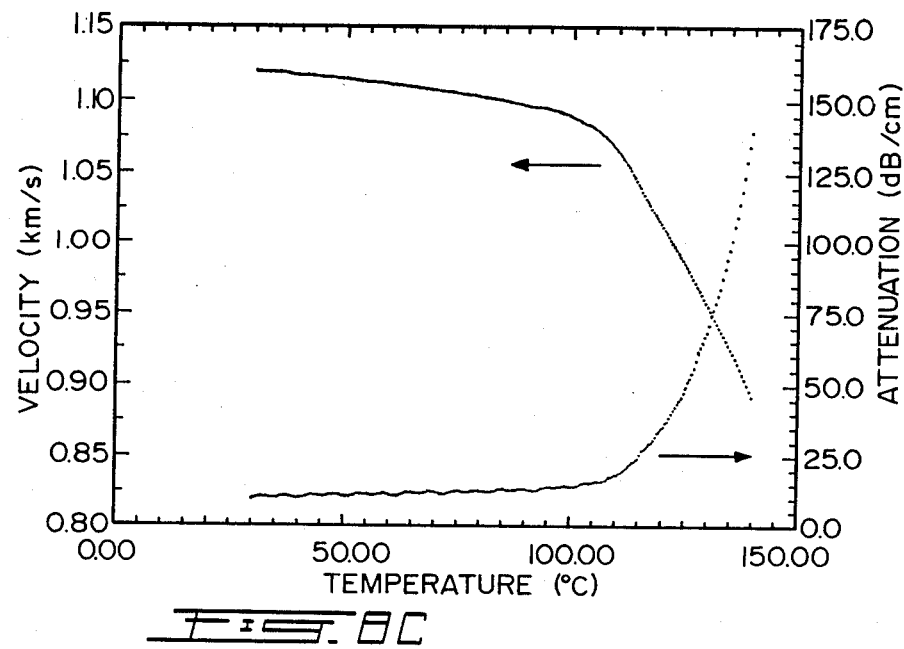
FIG. 8C is a plot of shear velocity and attenuation values against temperature, also obtained from data provided by the apparatus of FIG. 1.

FIG. 8C shows the corresponding temperature variation for the shear velocity $v_S$ and attenuation $A_S$. The knee in the velocity curve occurs at the glass transition temperature Tg. Hence, the measurement of shear velocity also provides for a very accurate determination of Tg. In the figure, it is seen that near 140° C. the attenuation rises sharply, indicating that in this region of temperature the polymer transforms into a liquid which does not transmit shear waves.

The results shown in FIGS. 8A, 8B, and 8C were obtained in simultaneity during the same experiment, by using an X-cut lithium niobate transducer to produce both longitudinal and shear waves.

Figure 9A:
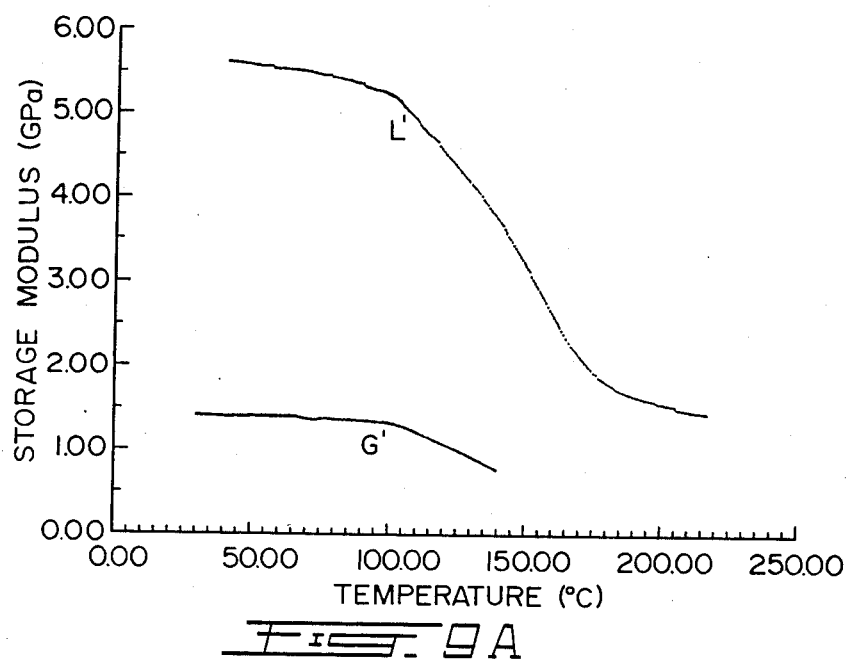
FIG. 9A is a plot showing the thermal variation of the longitudinal and shear storage moduli.

FIG. 9A illustrates how the data for the specific volume V (or density $\rho = 1/V$) in FIG. 8A, the longitudinal velocity $v_1$ and attenuation $A_1$ in FIG. 8B are used to compute the longitudinal storage modulus L', through the use of equation (19). Also illustrated is the manner in which the specific volume V (or density $\rho = 1/V$) in FIG. 8A, the shear velocity $v_S$ and attenuation $A_S$ in FIG. 8C are used to compute the shear storage modulus, G', through the use of equation (23).

Figure 9B:
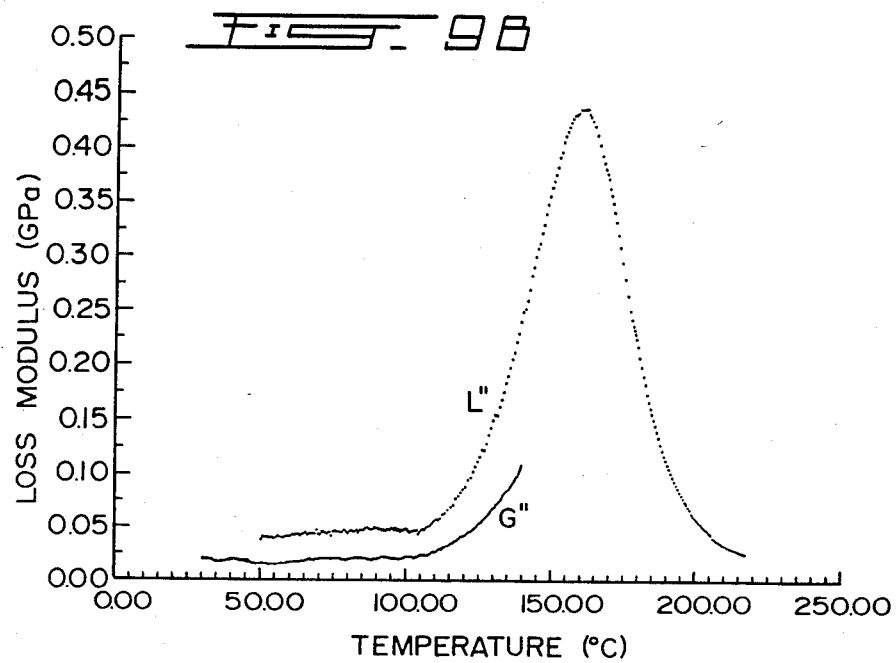
FIG. 9B is a plot showing the thermal variation of the longitudinal and shear loss moduli.

FIG. 9B illustrates how the data of FIGS. 8A, 8B and 8C can be used to compute the longitudinal loss modulus L", through the use of equation (20) and the shear loss modulus G", through the use of equation (24).

The results shown in FIGS. 9A and 9B illustrate how the technique allows for a complete characterization of the viscoelastic moduli of the polymer.

FIG. 10 shows how data such as those of FIGS. 8A, 8B and 8C obtained at different pressures (1) 130 bars, (2) 225 bars, (3) 270 bars, (4) 380 bars, (5) 520 bars, (6) 610 bars and (7) 715 bars can be used to compute the dynamic compressibility $\beta = 1/K'$, through the use of equations (19), (23) and (27). The technique thus allows for a complete characterization of the viscoelastic properties of polymers under pressure.

The results shown in FIG. 11 were obtained with the present technique on a sample of semicrystalline polypropylene. The frequency of the longitudinal waves was 2.5 MHz and the heating and cooling rates were 2° C./min.

Figure 11A:
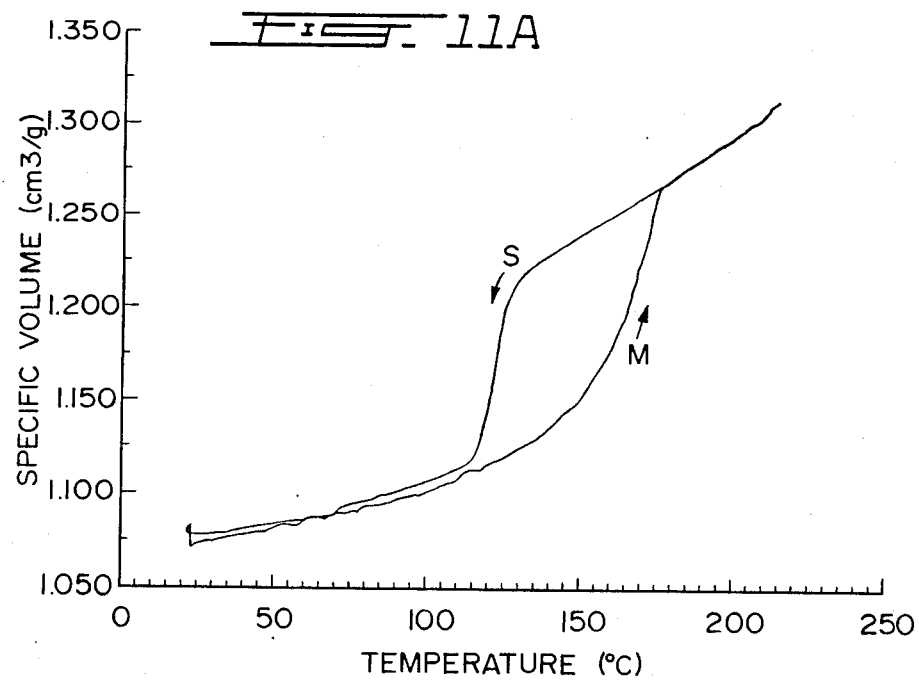
FIG. 11A which is on the same sheet of drawings as FIG. 9B is a plot showing the thermal variation of the specific volume on heating and cooling.

FIG. 11A shows the results obtained for the specific volume on heating (melting curve M) and cooling (solidification curve S). The knee in the melting curve corresponds to the melting temperature Tm, and that on the solidification curve corresponds to the solidification temperature Ts. The large difference that exists between Tm and Ts is characteristic of the dynamics for the crystallization of a very viscous liquid.

FIG. 11B shows the corresponding behaviour for the storage modulus L' obtained on heating (melting curve M) and cooling (solidification curve S). The knees that are seen in the curves correspond to the melting (Tm) and solidification (Ts) temperatures. The storage modulus serves to characterize the state of solidification for the polymer.

FIG. 11C shows the corresponding behaviour for the loss modulus L" obtained on heating (melting curve M) and cooling (solidification curve S). The maximum that occurs near 20° C. is related to the glass transition phenomenon and describes the related relaxation process. The knees that are seen at higher temperature correspond to the melting (Tm) and solidification (Ts) temperatures. The loss moduli is used to characterize the latent heat associated to the liquid-solid transition in semi-crystalline polymers.

We claim:

1. A method of ultrasonically characterizing polymer materials, which comprises the steps of:
   (a) holding a sample of a polymer in confinement between two axially aligned buffer rods having opposed parallel end surfaces spaced from one another to define a gap filled with the polymer sample, said polymer sample being acoustically coupled to said opposed end surfaces of said buffer rods;
   (b) transmitting ultrasonic waves through one of said buffer rods in a direction toward said polymer sample for interaction therewith;
   (c) subjecting said polymer sample to controlled temperature or pressure variations over a predetermined period of time, the variation in temperature or pressure being effected via said buffer rods;
   (d) continously monitoring phase and amplitude variations of the ultrasonic waves having interacted with said polymer sample while simultaneously monitoring thickness variations of said polymer sample, over said predetermined period of time, to obtain data comprising phase, amplitude and thickness values measured as a function of temperature or pressure and time; and
   (e) processing the data obtained in step (d) to derive characteristic parameters providing both a thermodynamic and viscoelastic characterization of said polymer.

2. A method as claimed in claim 1, wherein said polymer sample is subjected to controlled temperature variations while being maintained under a constant pressure.

3. A method as claimed in claim 1, wherein said polymer sample is subjected to controlled pressure variations while being maintained at a constant temperature.

4. A method as claimed in claim 1, wherein said polymer sample is subjected to controlled temperature and pressure variations.

5. A method as claimed in claim 1, wherein the temperature of said polymer sample is in the range of from about −105° C. to about 400° C.

6. A method as claimed in claim 1, wherein the pressure of said polymer sample is in the range of from about 1 bar to about 2000 bars.

7. A method as claimed in claim 1, wherein longitudinal or shear ultrasonic waves having a frequency ranging from about 0.5 to about 20 MHz are transmitted through said one buffer rod.

8. A method as claimed in claim 1, wherein both longitudinal and shear ultrasonic waves having a frequency ranging from about 0.5 to about 20 MHz are transmitted through said one buffer rod.

9. A method as claimed in claim 1, wherein said phase and amplitude monitoring is effected in reflection mode.

10. A method as claimed in claim 1, wherein said phase and amplitude monitoring is effected in transmission mode.

11. An apparatus for ultrasonically characterizing polymer materials, comprising:
   a pair of axially aligned buffer rods having opposed parallel end surfaces spaced from one another to define a gap for receiving a sample of a polymer;
   sample holding means for holding the polymer sample in confinement between said buffer rods while allowing compression or expansion of said polymer sample through axial displacement of said rods toward or away from one another, said polymer sample being acoustically coupled to said opposed end surfaces of said buffer rods;

rod alignment maintaining means for maintaining said buffer rods in alignment with one another while allowing relative axial displacement thereof, said rod alignment means including means allowing transmission of pressure through said rods to said polymer sample for subjecting the sample to controlled pressure variations;

temperature control means including constant temperature heat sink means thermally anchored with said buffer rods for subjecting said polymer sample to controlled temperature variations;

ultrasonic tranducer means acoustically coupled with one of said buffer rods for transmitting therethrough ultrasonic waves in a direction toward said polymer sample for interaction therewith;

first monitoring means for continously monitoring phase and amplitude variations of the ultrasonic waves having interacted with said polymer sample, over a predetermined period of time during which said polymer sample is subjected to said controlled temperature or pressure variations, to provide data comprising phase and amplitude values measured as a function of temperature or pressure and time;

second monitoring means for simultaneously monitoring thickness variations of said polymer sample, over said predetermined period of time, to provide data comprising thickness values measured as a function of temperature or pressure and time; and data processing means operatively connected to said first and second monitoring means for processing said data to derive characteristic parameters providing both a thermodynamic and viscoelastic characterization of said polymer.

12. An apparatus as claimed in claim 11, wherein said buffer rods are made of a material selected from the group consisting of stainless steel, high-stress-proof steel, titanium and titanium based alloys.

13. An apparatus as claimed in claim 11, wherein said buffer rods have equal lengths.

14. An apparatus as claimed in claim 11, wherein said buffer rods are each provided on a surface portion intermediate the ends thereof with V-shaped grooves defining a double helix pattern to thereby minimize undesirable effects caused by sound diffraction.

15. An apparatus as claimed in claim 11, wherein the other buffer rod is fixed and said one buffer rod is axially movable toward or away from said other buffer rod to vary the gap defined therebetween, and wherein said sample holding means comprises a hollow cylindrical member threadably engaged with said other buffer rod at the end thereof including said parallel end surface, said cylindrical member receiving therein said one buffer rod such that said end surface thereof faces said end surface of said other buffer rod while permitting free axial displacement of said one buffer rod relative to said other buffer rod, an annular cover threadably engaged with said cylindrical member and through which extends said one buffer rod, and sealing means arranged between said cylindrical member and said buffer rods for providing a leak tight seal at pressures up to about 2000 bars.

16. An apparatus as claimed in claim 15, wherein said sealing means include a sealing ring arranged between said cylindrical member and said one buffer rod, said sealing ring having a U-shaped cross-section defining an inner cavity and being radially expandable upon liquid polymer filling said cavity under pressure to provide a leak tight seal around said one buffer rod.

17. An apparatus as claimed in claim 11, wherein said temperature control means comprise two pairs of semicylindrical members made of thermally conductive material, each pair of members being interconnected together and receiving therebetween a respective one of said buffer rods for clamping engagement therewith, each said member being provided with heating and cooling means for heating and cooling said respective buffer rod to thereby heat or cool said polymer sample through two isothermal surfaces corresponding to said opposed end surfaces of said buffer rods.

18. An apparatus as claimed in claim 17, wherein each said buffer rod is provided adjacent the end thereof opposite said end surface with a plurality of spaced-apart annular grooves which are interconnected to define a circumferential channel for circulation of a cooling fluid, and wherein said heat sink means comprise two sleeve members each associated with a respective one of said buffer rods and sealingly arranged over said annular grooves thereof, said sleeve members having inlet and outlet means for circulating said cooling fluid through said channel to thereby maintain said ends of said buffer rods at a constant temperature.

19. An apparatus as claimed in claim 11, wherein said ultrasonic transducer means comprises a transducer mounted at the end of said one buffer rod opposite said end surface thereof, said transducer acting as both a transmitting and receiving transducer, and wherein said first monitoring means are operatively connected to said transmitting and receiving transducer for monitoring ultrasonic phase and amplitude variations in reflection mode.

20. An apparatus as claimed in claim 11, wherein said ultrasonic transducer means comprise a transmitting transducer mounted at the end of said one buffer rod opposite said end surface thereof and a receiving transducer mounted at the end of the other buffer rod opposite said end surface thereof, and wherein said first monitoring means are operatively connected to said transmitting and receiving transducers for monitoring ultrasonic phase and amplitude variations in transmission mode.

* * * * *